United States Patent [19]

Penrose et al.

[11] 4,186,264

[45] Jan. 29, 1980

[54] TRIAZAPENTADIENES AS ACARICIDES

[75] Inventors: Alexander B. Penrose, Tilmanstone, Nr. Deal; Michael R. G. Leeming, Canterbury, both of England

[73] Assignee: Pfizer Inc., New York, N.Y.

[21] Appl. No.: 943,665

[22] Filed: Sep. 18, 1978

Related U.S. Application Data

[62] Division of Ser. No. 787,084, Apr. 13, 1977, Pat. No. 4,128,652.

[30] Foreign Application Priority Data

Apr. 20, 1976 [GB] United Kingdom ............... 15812/76
Aug. 18, 1976 [GB] United Kingdom ............... 34319/76

[51] Int. Cl.$^2$ ............... A01N 9/12; C07D 275/02; C07D 275/04

[52] U.S. Cl. .................. 424/270; 542/417; 542/419

[58] Field of Search ............... 542/417, 419; 424/270

[56] References Cited

U.S. PATENT DOCUMENTS

4,011,343  3/1977  Leeming et al. ............... 424/326

FOREIGN PATENT DOCUMENTS

816760   4/1974  Belgium ............... 260/564
2405546  8/1975  Fed. Rep. of Germany .
1288811  9/1972  United Kingdom .
1327935  8/1973  United Kingdom .

*Primary Examiner*—Thomas A. Waltz
*Attorney, Agent, or Firm*—Connolly and Hutz

[57] ABSTRACT

Certain heteroaryl triazapentadienes with acaricidal properties and their preparation are described.

8 Claims, No Drawings

TRIAZAPENTADIENES AS ACARICIDES

CROSS REFERENCE TO RELATED APPLICATION

This application is a division of application Ser. No. 787,084 filed Apr. 13, 1977, now U.S. Pat. No. 4,128,652.

BACKGROUND OF THE INVENTION

All stages in the life cycle of ticks tend to damage the skins of afflicted animals and thereby spoil the state of the skins with the consequence that cattle hides and sheep skins intended for the manufacture of leather and sheep skin are reduced in quality. Furthermore, the ticks may facilitate the transmission of disease to the afflicted animal, and the general state of health and the quality of flesh of the animal may be detrimentally affected.

Belgian Pat. No. 816,760 describes certain 5-(substituted phenyl)-3-(alkyl)-1-(alkyl)-1,3,5-triazapenta-1,4-dienes as broad spectrum parasiticides.

We have now found that certain 5-(substituted phenyl)-3-methyl-1-(heteroaryl)-triazapenta-1,4-dienes have particularly useful acaricidal properties, and are thus very useful in destroying one or more stages in the life cycle of ticks which tend to infest the skins of animals such as cattle. They may also have insecticidal properties, particularly against plant insects such as pea aphids (hemiptera).

SUMMARY OF THE INVENTION

This invention is concerned with triazapentadienes of the formula:

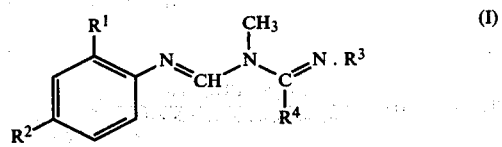

wherein
$R^1$ is a $C_1$-$C_4$ alkyl group;
$R^2$ is a hydrogen atom, a halogen atom or a $C_1$-$C_4$ alkyl group;
$R^3$ is a monocyclic or bicyclic heteroaryl group attached to the adjacent nitrogen atom by a carbon atom of said group; and
$R^4$ is a hydrogen atom or a $C_1$-$C_4$ alkyl group;
and the acid addition salts of the compounds of the formula (I) which form such salts.

DETAILED DESCRIPTION OF THE INVENTION

In this specification the term "halogen" means fluorine, chlorine, bromine or iodine.

Alkyl groups containing three or more carbon atoms may be straight or branched chain. The preferred alkyl groups contain 1 or 2 carbon atoms.

$R^1$ is preferably a methyl group.
$R^2$ is preferably a methyl group or a chlorine atom.
$R^2$ is most preferably methyl.

Generally, the preferred heteroaryl groups within the scope of $R^3$ are those including at least one ring nitrogen atom, such as quinolyl, isoquinolyl, pyridyl, pyrimidinyl, quinazolinyl, quinoxalinyl, tetrazolyl, thiazolyl, benzothiazolyl, 4,5,6,7-tetrahydrobenzothiazolyl, thiadiazolyl, indazolyl, oxazolyl, benzoxazolyl, pyridazinyl and pyrazinyl. However, benzothienyl is also a preferred heteroaryl group within the scope of $R^3$.

The heteroaryl group represented by $R^3$ may be substituted or unsubstituted. Preferred substituents are $C_1$-$C_6$ alkyl, $C_1$-$C_6$ alkoxy, di($C_1$-$C_4$ alkoxy) methyl, ($C_1$-$C_4$ alkoxy) carbonyl, halogen, trifluoromethyl, phenyl, and $C_2$-$C_5$ alkanoyl. Preferred alkoxy groups contain 1 or 2 carbon atoms and preferred alkanoyl groups 2 or 3 carbon atoms.

The more preferred heteroaryl groups are quinolyl, isoquinolyl, pyridyl, quinoxalinyl, pyridazinyl, pyrimidinyl, pyrazinyl, indazolyl, tetrazolyl, thiazolyl, benzothiazolyl, 4,5,6,7-tetrahydrobenzothiazolyl and benzothienyl optionally containing one or two substituents selected from $C_1$-$C_4$ alkyl, $C_1$-$C_4$ alkoxy, phenyl, di($C_1$-$C_4$ alkoxy) methyl, ($C_1$-$C_4$ alkoxy)carbonyl and halogen.

The most preferred heteroaryl groups are thiazolyl, pyridyl, quinolyl, pyrazinyl, pyridazinyl, quinoxalinyl, benzothiazolyl and benzothienyla optionally containing one or two substituents selected from halogen, $C_1$-$C_4$ alkyl and $C_1$-$C_4$ alkoxy.

$R^4$ is preferably a hydrogen atom.

The preferred individual compounds are as follows:

5-(2,5-dimethylphenyl)-3-methyl-1-(2-thiazolyl)-1,3,5-triazapenta-1,4-diene 5-(2,4-dimethylphenyl)-3-methyl-1-(2-pyridyl)-1,3,5-triazapenta-1,4-diene 5-(2,4-dimethylphenyl)-3-methyl-1-(3-quinolyl)-1,3,5-triazapenta-1,4-diene 5-(2,4-dimethylphenyl)-3-methyl-1-(3-ethyl-6-methyl-pyrid-2-yl)-1,3,5-triazapenta-1,4-diene 5-(2,4-dimethylphenyl)-3-methyl-1-(3-ethyl-pyrid-2-yl)-1,3,5-triazapenta-1,4-diene 5-(2,4-dimethylphenyl)-3-methyl-1-(3-methyl-pyrid-2-yl)-1,3,5-triazapenta-1,4-diene 5-(2,4-dimethylphenyl)-3-methyl-1-(2,5-dimethyl-pyrid-3-yl)-1,3,5-triazapenta-1,4-diene 5-(2,4-dimethylphenyl)-3-methyl-1-(2-chloro-pyrid-3-yl)-1,3,5-triazapenta-1,4-diene 5-(2,4-dimethylphenyl)-3-methyl-1-(2-pyrazinyl)-1,3,5-triazapenta-1,4-diene 5-(2,4-dimethylphenyl)-3-methyl-1-(6-methoxy-pyridazin-3-yl)-1,3,5-triazapenta-1,4-diene 5-(2,4-dimethylphenyl)-3-methyl-1-(6-quinolyl)-1,3,5-triazapenta-1,4-diene 5-(2,4-dimethylphenyl)-3-methyl-1-(6-quinoxalinyl)-1,3,5-triazapenta-1,4-diene 5-(2,4-dimethylphenyl)-3-methyl-1-(3,6-dimethyl-pyrid-2-yl)-1,3,5-triazapenta-1,4-diene 5-(2,4-dimethylphenyl)-3-methyl-1-(3,5-dimethyl-pyrid-2-yl)-1,3,5-triazapenta-1,4-diene 5-(2,4-dimethylphenyl)-3-methyl-1-(3-n-propyl-pyrid-2-yl)-1,3,5-triazapenta-1,4-diene 5-(2,4-dimethylphenyl)-3-methyl-1-(3-n-butyl-pyrid-2-yl)-1,3,5-triazapenta-1,4-diene 5-(2,4-dimethylphenyl)-3-methyl-1-(6-benzothiazolyl)-1,3,5-triazapenta-1,4-diene 5-(2,4-dimethylphenyl)-3-methyl-1-(6-benzothienyl)-1,3,5-triazapenta-1,4-diene 5-(2,4-dimethylphenyl)-3-methyl-1-(3,4-dimethyl-pyrid-2-yl)-1,3,5-triazapenta-1,4-diene.

The compounds of the invention may be prepared via a number of routes, including the following:

(1) Compounds in which $R^4$ is hydrogen may be prepared by reacting a formamidine of the formula:

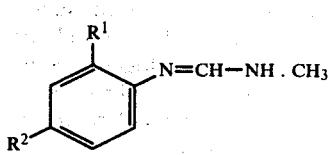

with an isonitrile of the formula $R^3.NC$. $R^1$, $R^2$ and $R^3$ are as defined for formula (I).

The reaction may be effected in the presence of a suitable catalyst, most preferably finely divided copper metal or a cuprous catalyst such as cuprous oxide or cuprous chloride in a trace amount, a typical reaction temperature being 50° to 80° C. Increased reaction temperatures are not generally recommended because they tend to increase the formation of by-products due to the reaction of one molecule of compound (II) with another such molecule. The reaction may be effected in the presence of a suitable inert organic solvent, such as benzene or toluene.

Generally, long reaction times are necessary unless finely divided copper metal is used as the catalyst.

Typically, the product is recovered by evaporation of the reaction mixture in vacuo to leave an oil which may, if necessary, be purified by a conventional procedure such as treatment with neutral alumina in 40°-60° petroleum ether. The purified oil may crystallise on standing to give crystals of the desired product of the formula (I).

The isonitriles of the formula $R^3.NC$ and the formamidines of the formula (II) are either known compounds or may be prepared by procedures analogous to those of the prior art. Methods for the preparation of formamidines falling within the formula (II) are described for example in British Patent Specifications Nos. 964,640, 1,039,930 and 1,327,936.

(2) The following route, in which $R^4$ may be hydrogen or $C_1-C_4$ alkyl, is also possible:

an imidate of the formula:

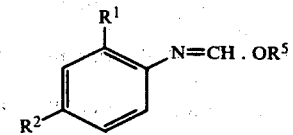

wherein $R^1$ and $R^2$ are as defined for formula (I) and $R^5$ is a $C_1-C_4$ alkyl group, is reacted with an amidine of the formula:

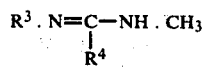

wherein $R^3$ and $R^4$ are as defined for formula (I).

(3) Compounds of the formula (I) in which $R^4$ is a hydrogen atom or a $C_1-C_4$ alkyl group may be prepared by reacting an amidine of the formula:

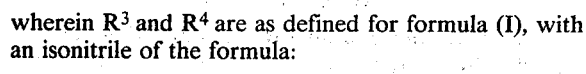

wherein $R^3$ and $R^4$ are as defined for formula (I), with an isonitrile of the formula:

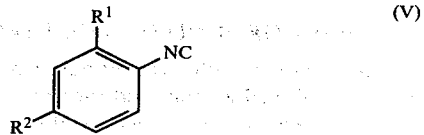

wherein $R^1$ and $R^2$ are as defined for formula (I).

The reaction and isolation of the product may be carried out in a similar manner to method (1) above, although in this case it is generally possible to use reaction temperature of above 80° C. without substantially increasing the formation of by-products, reaction generally being substantially complete within 4-8 hours at 100° C. except when using finely divided copper metal as the catalyst in which case the reaction is generally complete in 1-2 hours.

This is a preferred route. The starting materials of the formula (IV) are either known compounds or may be obtained in a conventional manner, e.g. as follows:

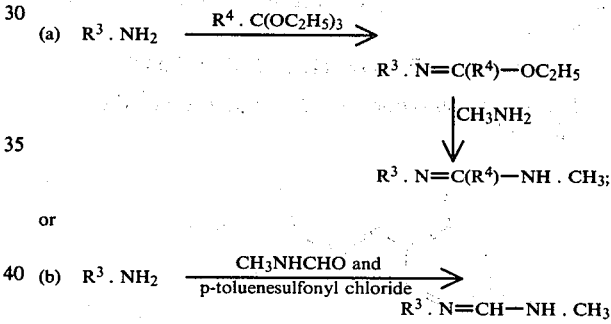

(4) The compounds of the formula (I) in which $R^4$ is a hydrogen atom or a $C_1-C_4$ alkyl group may also be prepared by reacting a formamidine of the formula:

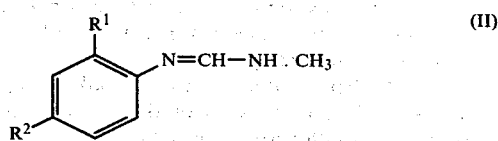

wherein $R^1$ and $R^2$ are as defined for formula (I), with an imidate of the formula:

wherein $R^3$ and $R^4$ are as defined for formula (I) and $R^6$ is a $C_1-C_4$ alkyl group. $R^6$ is preferably an ethyl group.

The reaction is typically carried out by heating the reactants together for several hours, e.g. at 40°-100° C. for 2-4 hours. Alternatively a solvent, e.g. iso-octane, may be used. The product typically crystallises on cooling and may be purified by crystallisation from e.g. hexane, cyclohexane or mixed solvents, e.g. methylene chloride/hexane. Treatment with decolouring carbon during crystallisation may be beneficial.

This is a preferred route.

The imidates of the formula (VI) are either known compounds or may be obtained in a conventional manner, e.g. as follows:

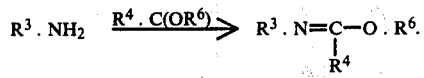

(5) The acid-addition salts of the compounds of the formula (I) which form such salts may be made in a conventional manner, e.g. by mixing a solution of the free base in a suitable solvent, e.g. diethyl ether, with a solution of the appropriate acid in a suitable solvent, e.g. diethyl ether, and recovering the salt as a precipitate.

The compounds of the formula (I) have acaricidal activity, particularly against all stages in the life cycle, including gravid female ticks, of the cattle ticks *Boophilus microplus*, *Haemaphysalis longicornus*, *Phipicephalus appendiculatus* and *Boophilus decoloratus*.

In one test, five freshly collected, fully engorged *Boophilus microplus* adult female ticks are used for each acaricidal compound. Using a micro-pipette 10 microliters of a solution containing 10 micro-grams of the acaricidal compound in ethanol or acetone, is applied to the dorsal surface of each of the ticks. The treated ticks are placed in weighed 1"×2" glass vials, weighed and stored at 26° C. and 80%+R.H. in plastic boxes for two weeks. The ticks are then removed from the vials and the vials weighed to give the weight of eggs laid by the ticks. Any reduction in the egg laying of the treated ticks is calculated as a percentage of the eggs laid by untreated control ticks.

The eggs are returned to the incubator for a further 3 weeks after which time the percentage of eggs hatching is estimated.

The percentage reduction in the anticipated reproduction of the ticks is calculated using the weight of eggs laid and the percentage of eggs hatching.

The test may be repeated using smaller amounts of the acaricidal compound.

In another test, using a pipette 0.5 ml of a solution containing 0.5 mg of the acaricidal compound in ethanol or acetone is spread evenly on to a Whatman No. 1 filter paper 8 cm×6.25 cm (50 sq. c.m.) to give a dosage of 100 mg/m².

The treated paper is allowed to dry at room temperature, folded with the treated surface inside and two short edges sealed with a crimping machine. The open ended envelope is placed in a 1 lb Kilner jar containing damp cotton wool in a plastic pot and stored in an incubator at 26° C. for 24 hours. 20-50 *Boophilus microplus* larvae, which had hatched 8-14 days previously, are placed in the envelope using a small spatula. The open end is then crimped to form a sealed packet. The treated paper containing the larvae is returned to the Kilner jar and kept for a further 48 hours in the incubator. 20-50 larvae are placed similarly in an untreated paper envelope to act as controls. At the end of the 48 hour test period the mortality is noted and recorded as a percentage after correction for any mortality among the untreated control ticks.

The test may be repeated using smaller amounts of the acaricidal compound.

In addition to percentage effectiveness figures, $ED_{50}$ results can be obtained from dose response measurements using any of the afore-described tests.

Activity against *Haemaphysalis longicornus* nymphs may be measured in a similar manner to the above larvae test.

The activity of certain of the compounds of the Examples detailed hereinafter against the tick *Boophilus microplus* is set out in the following Table:

TABLE

| | Boophilus Microplus (in vitro) | | | |
|---|---|---|---|---|
| | Larva (Contact) | | Adult (Topical) | |
| Compound No. | Dose (mg/m²) | % Kill | Dose (µg/tick) | % Reduction in Egg Hatch |
| 1 | 100 | 100 | 10 | 100 |
| and 90 | 12.5 | 100 | 2 | 99 |
| 2 | 100 | 100 | 10 | 99 |
| and 91 | 6.25 | 100 | 4 | 93 |
| 3 | 100 | 100 | 10 | 99 |
| | 12.5 | 94 | 2 | 96 |
| 4 | 100 | 100 | 10 | 100 |
| | 12.5 | 100 | 2 | 97 |
| 5 | 100 | 100 | 10 | 100 |
| | 12.5 | 100 | 4 | 88 |
| 6 | 100 | 100 | 10 | 100 |
| | 6.25 | 100 | 4 | 86 |
| 7 | 100 | 100 | 10 | 89 |
| | 12.5 | 100 | | |
| 8 | 100 | 100 | 10 | 90 |
| | 25 | 100 | | |
| 9 | 100 | 100 | 10 | 53 |
| | 25 | 86 | | |
| 10 | 100 | 100 | 10 | 92 |
| | 25 | 89 | | |
| 11 | 100 | 100 | 10 | 92 |
| | 6.25 | 100 | | |
| 12 | 100 | 78 | — | — |
| 13 | 100 | 31 | 8 | 68 |
| 14 | 100 | 100 | 10 | 100 |
| | 3.13 | 90 | 4 | 97 |
| 15 | 100 | 100 | 10 | 100 |
| | 3.13 | 100 | 4 | 83 |
| 16 | 100 | 100 | 10 | 100 |
| and 92 | 3.13 | 98 | 2 | 95 |
| 17 | 100 | 100 | 10 | 100 |
| | 6.25 | 100 | 2 | 67 |
| 18 | 100 | 56 | 10 | 100 |
| and 76 | | | 4 | 99 |
| 20 | 100 | 100 | 10 | 29 |
| | 12.5 | 100 | | |
| 21 | 100 | 86 | 10 | 58 |
| 22 | 100 | 90 | 10 | 99 |
| | | | 4 | 97 |
| 23 | 100 | 100 | 10 | 85 |
| | 12.5 | 100 | | |
| 24 | 100 | 100 | 10 | 100 |
| | 12.5 | 83 | 2 | 90 |

TABLE-continued

| | Boophilus Microplus (in vitro) | | | |
|---|---|---|---|---|
| | Larva (Contact) | | Adult (Topical) | |
| Compound No. | Dose (mg/m$^2$) | % Kill | Dose (μg/tick) | % Reduction in Egg Hatch |
| 25 | 100 | 100 | 10 | 100 |
|    | 12.5 | 88 | 2 | 91 |
| 26 | 100 | 100 | 10 | 100 |
|    | 25 | 98 | 8 | 98 |
| 27 | 100 | 85 | 10 | 53 |
| 28 | 100 | 100 | 10 | 100 |
|    | 50 | 98 | 2 | 99 |
| 29 | 100 | 100 | 2 | 20 |
|    | 50 | 82 | | |
| 30 | 100 | 100 | 10 | 78 |
|    | 25 | 92 | | |
| 31 | 100 | 100 | 10 | 94 |
|    | 6.25 | 83 | | |
| 32 | 100 | 17 | 10 | 59 |
| 33 | 100 | 33 | 10 | 100 |
|    | | | 4 | 98 |
| 34 | 100 | 100 | 10 | 93 |
| 35 | 100 | 100 | 10 | 13 |
|    | 25 | 83 | | |
| 36 | 100 | 100 | 10 | 16 |
| 37 | 100 | 32 | 10 | 100 |
|    | | | 4 | 90 |
| 38 | 100 | 100 | 10 | 72 |
|    | 6.25 | 94 | | |
| 39 | 100 | 100 | 10 | 96 |
|    | 12.5 | 98 | | |
| 40 | 100 | 14 | 8 | 100 |
|    | | | 4 | 81 |
| 41 | 100 | 100 | 10 | 100 |
| 42 | 100 | 100 | 10 | 25 |
|    | 12.5 | 100 | | |
| 43 | 100 | 97 | 10 | 100 |
|    | 12.5 | 100 | | |
| 44 | 100 | 100 | 10 | 97 |
|    | 6.25 | 84 | | |
| 45 | 100 | 100 | 10 | 100 |
|    | 6.25 | 100 | | |
| 46 | 100 | 100 | 10 | 22 |
| 47 | 100 | 100 | 10 | 28 |
| 48 | 100 | 92 | 10 | 100 |
|    | | | 8 | 91 |
| 50 | 100 | 100 | 10 | 95 |
|    | 25 | 100 | 8 | 94 |
| 51 | 100 | 100 | 10 | 93 |
| 52 | 100 | 100 | 10 | 18 |
|    | 50 | 100 | | |
| 54 | 100 | 80 | 10 | 55 |
| 55 | 100 | 100 | 10 | 26 |
|    | 12.5 | 100 | | |
| 56 | 100 | 100 | 10 | 85 |
|    | 25 | 73 | | |
| 57 | 100 | 80 | 10 | 89 |
| 58 | 100 | 97 | 10 | 96 |
|    | 25 | 79 | | |
| 59 | 100 | 100 | 10 | 66 |
|    | 25 | 68 | | |
| 60 | 100 | 94 | 10 | 28 |
|    | 25 | 88 | | |
| 62 | 100 | 98 | 10 | 88 |
|    | 50 | 60 | | |
| 63 | 100 | 100 | 10 | 7 |
|    | 12.5 | 100 | | |
| 65 | 100 | 100 | 10 | 100 |
|    | 12.5 | 76 | 1 | 97 |
| 66 | 100 | 100 | 10 | 100 |
|    | | | 1 | 90 |
| 67 | 100 | 84 | 10 | 98 |
|    | | | 4 | 58 |
| 68 | 100 | 69 | 10 | 100 |
|    | | | 4 | 84 |
| 69 | 100 | 24 | 10 | 99 |
| 70 | 100 | 100 | 10 | 100 |
|    | 3.12 | 95 | 1 | 31 |
| 71 | 100 | 85 | 10 | 89 |
|    | | | 4 | 57 |
| 72 | 100 | 100 | 10 | 99 |
|    | 1.56 | 73 | 2 | 22 |
| 73 | 100 | 100 | 10 | 91 |
|    | 12.5 | 100 | 2 | 69 |
| 74 | 100 | 66 | 10 | 99 |
|    | | | 4 | 52 |
| 77 | 100 | 100 | 10 | 100 |
|    | 12.5 | 89 | 2 | 71 |
| 78 | 100 | 91 | 10 | 100 |
|    | | | 2 | 97 |
| 79 | 100 | 100 | 10 | 100 |
|    | 50 | 33 | 1 | 83 |
| 80 | 100 | 59 | 10 | 100 |
|    | | | 2 | 98 |
| 83 | 100 | 85 | 10 | 100 |
|    | | | 1 | 97 |

Thus the invention also provides an acaricidal composition comprising a compound of the formula (I) together with a diluent or carrier. The diluent or carrier may be a solid or a liquid, optionally together with an antioxidant, dispersing agent, emulsifying agent or wetting agent. The compositions of the invention include not only compositions in a suitable form for application but concentrated primary compositions which may be supplied to the user and which require dilution with a suitable quantity of water or other diluent prior to application. Typical compositions of the invention include, for example, dusting powders, dispersible powders, dispersions, emulsions and emulsifiable concentrates.

A dust may be made by mixing the appropriate amount of the finely divided active compound with a solid pulverent diluent or carrier such as talc, clay, calcite, pyrophyllite, diatomaceous earth, walnut shell flour, silica gel, hydrated alumina, or calcium silicate. As an alternative method of preparation, the diluent or carrier is mixed with a solution of the active compound in a volatile organic solvent such as benzene, the solvent being subsequently removed by evaporation. Typically, the active compound will be present in the dust in an amount of from 0.25 to about 4% by weight.

Dispersible powders may be made by adding a suitable dispersing agent to the active compound, or to a dust containing the active compound, so that a stable aqueous dispersion of the active compound is formed on mixing the powder with water. The dispersible powders preferably contain from about 25 to 75% by weight of the active compound.

Emulsifiable concentrates comprise a solution of the active compound in a substantially water-immiscible non-toxic organic solvent containing an emulsifying agent. Suitable solvents include, for example, toluene, xylene, petroleum oil, and alkylated naphthalenes. Preferably, the concentrate will contain 5–75 gms. of the active compound per 100 ml. of solution. The concentrates may be diluted with water prior to use to give a typical concentration of the active compound in the aqueous medium of from e.g. about 0.001 to about 0.1% w/v (g/100 ml.), or approximately 10 to 1000 p.p.m. The volatile solvents, e.g. toluene and xylene, evaporate after spraying to leave a deposit of the active ingredient. The made up spray or dip will generally be an emulsion.

The compositions of the invention may be applied to ground, such as that around dairies, in order to combat e.g. cattle ticks thereon. However, it is preferred to treat animals by spraying them or passing them through animal dips.

Thus the present invention also provides a method for protecting animals, particularly cattle, from acarids, particularly cattle ticks, which comprises treating the animal externally with an acaricidal amount of a compound of the formula (I) or acaricidal composition as defined above.

The compositions of the invention may also contain a pesticide, fungicide, additional acaricide, or the like.

The invention is illustrated by the following Examples, in which all temperatures are given in °C. The compounds of the invention were characterised by infra-red and nuclear magnetic resonance (n.m.r.) spectra, thin layer chromatography, and, in most cases, by melting point, analytical and mass spectral data. In the n.m.r. data, the protons responsible for the signals are underlined, s, q, t and m indicating, respectively, a singlet, quartet, triplet and multiplet.

EXAMPLE 1

Preparation of 5-(2,4-dimethylphenyl)-3-methyl-1-(2-pyridyl)-1,3,5-triazapenta-1,4-diene

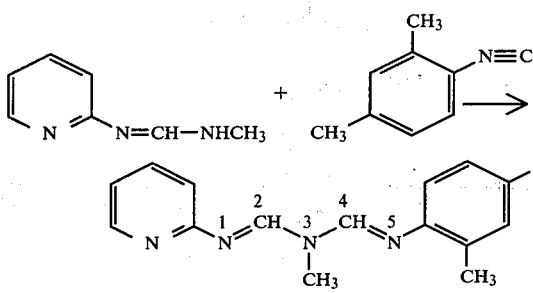

A mixture of N-methyl-N'-(2-pyridyl)-formamidine (2.5 g, 0.0185 m), 2,4-dimethylphenylisocyanide (2.4 g, 0.0185 m), cuprous oxide (trace amount) and dry toluene (60 ml) was heated on a steam bath with occasional agitation for 4 hours. The reaction mixture was then cooled, filtered through "Hyflo" (diatomaceous earth) and alumina, and the toluene filtrate evaporated to dryness in vacuo to yield a viscous oil. The oil was triturated with 60°–80° petroleum ether to yield a white solid. Crystallisation of this solid from ether/60°–80° petroleum ether yielded the product, 5-(2,4-dimethylphenyl)-3-methyl-1-(2-pyridyl)-1,3,5-triazapenta-1,4-diene, (1.0 g) m.p. 100°.

Analysis %: Found: C, 71.84% H, 6.52; H, 20.59. $C_{16}H_{18}N_4$ requires: C, 72.15; H, 6.81; H, 21.04.

EXAMPLES 2 TO 75

The following compounds were prepared by procedures similar to that of Example 1, starting from 2,4-dimethylphenylisocyanide or 4-chloro-2-methylphenylisocyanide and the appropriate amidine of the formula $R^3.N{=}C(R^4).NHCH_3$.

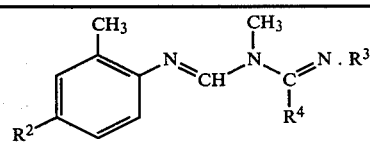

| Compound No. | $R^2$ | $R^3$ | $R^4$ | m.p. (°C.) | C | H | N |
|---|---|---|---|---|---|---|---|
| | | | | | (Theoretical in brackets) | | |
| | | | | | (or n.m.r. and mass spectral data) | | |
| 2 | $CH_3$ | ![quinolinyl] | H | 76–79 | 71.68 (71.83 | 6.71 6.63 | 16.88 16.75)* |
| 3 | $CH_3$ | ![pyridyl] | H | 86–88 | 71.79 (72.15 | 6.96 6.81 | 20.36 21.07) |

-continued

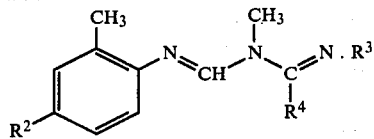

| | R² | R⁴ | R³ | m.p. (°C) | C | H | N |
|---|---|---|---|---|---|---|---|
| 4 | CH₃ | 2,6-dimethylpyridin-4-yl | H | 115–116 | 73.00 (73.44 | 7.45 7.53 | 18.76 19.03) |
| 5 | CH₃ | 2-chloropyridin-4-yl | H | 98 | 63.77 (63.87 | 5.51 5.78 | 18.85 18.63) |

*this compound was isolated as the monohydrate, and the theoretical analysis calculated accordingly.

| | R² | R⁴ | R³ | m.p. (°C) | C | H | N |
|---|---|---|---|---|---|---|---|
| 6 | CH₃ | pyridin-4-yl | H | 104–5 | 71.98 (72.15 | 6.79 6.81 | 20.97 21.07) |
| 7 | Cl | pyridin-4-yl | H | 112 | 62.64 (62.82 | 5.12 5.27 | 19.19 19.54) |
| 8 | Cl | pyridin-3-yl | H | 138–140 | 63.02 (62.82 | 5.11 5.27 | 19.27 19.54) |
| 9 | Cl | 2-chloropyridin-4-yl | H | 84–86 | 56.05 (56.09 | 4.04 4.39 | 17.30 17.44) |
| 10 | Cl | 2,6-dimethoxypyridin-4-yl | H | 93–96 | 58.72 (58.87 | 5.50 5.52 | 15.93 16.16) |
| 11 | Cl | pyridin-2-yl | H | 75–79 | 62.70 (62.82 | 5.35 5.27 | 20.09 19.54) |
| 12 | CH₃ | pyridin-3-yl | CH₃ | oil | n.m.r.(CDCl₃):δ = 2.10(s,—C(CH₃)—); 2.32(s, 2 CH₃ groups on benzene ring; 3.53(s, —N(CH₃)—); 8.35(s, —N=CH—N) Molecular wt. from mass spectral data 280. | | |
| 13 | CH₃ | pyridin-3-yl | C₂H₅ | oil | n.m.r. (CDCl₃): δ = 1.15(t,—CH₂CH₃) 2.32 (s,2 CH₃ groups on benzene ring; 2.53 (q,—CH₂CH₃; 3.53(s, —N(CH₃)—); 8.35 (s,—N=CH—N). Molecular weight from mass spectral data 294. | | |
| 14 | CH₃ | 5-chloropyridin-2-yl | H | 125 | 64.15 (63.90 | 5.63 5.66 | 18.68 18.64) |

-continued

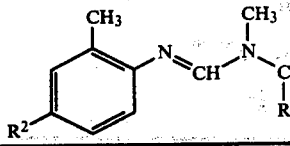

| Compound No. | R² | R³ | R⁴ | m.p. (°C.) | C (or n.m.r.) | H | N |
|---|---|---|---|---|---|---|---|
| 15 | Cl | [5-chloropyridin-2-yl] | H | 152 | 56.49 (56.07 | 4.44 4.36 | 17.78 17.45) |
| 16 | CH₃ | [3-ethyl-6-methylpyridin-2-yl] | H | 80 | 74.08 (74.00 | 7.89 7.84 | 18.11 18.17) |
| 17 | Cl | [3-ethyl-6-methylpyridin-2-yl] | H | 85 | 65.61 (65.74 | 6.49 6.44 | 16.91 17.04) |
| 18* | CH₃ | [thiazol-2-yl] | H | 99–100 | 61.36 (61.74 | 5.81 5.92 | 21.18 20.57) |

*This experiment was repeated under similar conditions but using a trace amount of finely-divided copper metal in place of cuprous oxide as the catalyst.

| Compound No. | R² | R³ | R⁴ | m.p. (°C.) | C (or n.m.r.) | H | N |
|---|---|---|---|---|---|---|---|
| 19 | CH₃ | [benzothiazol-2-yl] | H | 133–136 | 67.72 (67.05 | 5.69 5.63 | 17.52 17.38) |
| 20 | CH₃ | [2,6-dichloropyridin-3-yl] | H | 151–153 | 57.01 (57.32 | 4.85 4.81 | 16.72 16.71) |
| 21 | CH₃ | [4-methyl-5-phenylthiazol-2-yl] | H | 129–131 | 69.40 (69.58 | 6.11 6.12 | 15.50 15.46) |
| 22 | CH₃ | [quinolin-6-yl] | H | 96–98 | 76.02 (75.92 | 6.32 6.37 | 17.85 17.71) |
| 23 | Cl | [quinolin-6-yl] | H | 110 | 67.88 (67.75 | 5.01 5.09 | 16.75 16.63) |
| 24 | CH₃ | [2,4,6-trimethylpyridin-3-yl] | H | 129–130 | 73.25 (73.44 | 7.53 7.53 | 19.25 19.03) |

4,186,264

-continued $$\underset{R^2}{\text{CH}_3\text{-substituted aryl}}-N=CH-N(CH_3)-C(R^4)=N-R^3$$

| No. | $R^2$ | Heterocycle | $R^3$ | m.p. (°C) | C % found (calc) | H % found (calc) | N % found (calc) |
|---|---|---|---|---|---|---|---|
| 25 | $CH_3$ | quinoxalin-2-yl | H | 104–5 | 71.85 (71.90 | 5.88 6.03 | 21.53 22.07) |
| 26 | Cl | quinoxalin-2-yl | H | 132–4 | 63.89 (64.00 | 4.78 4.77 | 20.67 20.73) |
| 27 | $CH_3$ | 2,6-dimethylpyridin-4-yl | $CH_3$ | 76–8 | 73.77 (73.99 | 7.75 7.84 | 18.02 18.17) |
| 28 | $CH_3$ | 6-methoxy-3-pyridazinyl | H | 150–151 | 64.59 (64.63 | 6.30 6.44 | 23.03 55) |
| 29 | Cl | pyridin-3-yl | $CH_3$ | Oil | n.m.r. (CDCl$_3$) $\delta$ = 3.55 (s, —N—CH$_3$), 2.15 (s, —C(CH$_3$)=N—) | | |
| 30 | Cl | thiazol-2-yl | H | 62–4 | 53.22 (53.33 | 4.52 4.48 | 19.52 19.14) |
| 31 | Cl | pyrazin-2-yl | H | 128–9 | 58.24 (58.44 | 4.88 4.90 | 24.16 24.34) |
| 32 | $CH_3$ | 2,6-dimethoxy-3-methylpyridin-4-yl | $CH_3$ | 100–101 | 67.24 (67.04 | 7.07 7.11 | 16.52 16.46) |
| 33 | Cl | benzothiazol-2-yl | H | 130–131 | 59.52 (59.56 | 4.39 4.41 | 16.40 16.34) |
| 34 | Cl | 6-methylpyridin-2-yl | $C_2H_5$ | 70 | 64.71 (64.86 | 6.09 6.08 | 17.40 .80) |
| 35 | $CH_3$ | 6-methylpyridin-2-yl | $CH_3$ | 142 | 72.86 (72.83 | 7.28 7.19 | 20.18 19.98) |

-continued

Structure:
2-methyl-4-R² phenyl—N=CH—N(CH₃)—C(R⁴)=N·R³

| No. | R² | (group) | R⁴ | m.p./yield | C found (calc) | H found (calc) | N found (calc) |
|---|---|---|---|---|---|---|---|
| 36 | Cl | 6-methylpyridin-2-yl | CH₃ | 97 | 63.63 (63.89 | 5.76 5.57 | 18.74 18.63) |
| 37 | CH₃ | 3-methylpyrazin-2-yl | H | 129–130 | 67.41 (67.19 | 6.23 6.41 | 25.56 26.20) |
| 38 | Cl | 6-methoxy-3-methylpyridazin-3-yl | H | 148 | 56.29 (56.69 | 5.01 5.07 | 21.83 22.04) |
| 39 | CH₃ | pyridin-2-yl | C₂H₅ | 85 | 73.16 (73.44 | 7.70 7.53 | 18.75 19.03) |
| 40 | CH₃ | 1-(diethoxymethyl)-5-methylbenzimidazol-2-yl | H | 69–72 | 67.45 (67.79 | 7.07 7.17 | 17.40 17.50) |
| 41 | Cl | 1-(diethoxymethyl)-5-methylbenzimidazol-2-yl | H | Oil | n.m.r. (CDCl₃) δ=3.5 (s, —N—CH₃); 1.2 (t, [O—CH₂CH₃]₂); 3.6 (q, [O—CH₂CH₃]₂) | | |
| 42 | CH₃ | 4-phenylthiazol-2-yl | H | 134–5 | 68.57 (68.94 | 5.90 5.79 | 15.96 16.08) |
| 43 | CH₃ | 4-methylthiazol-2-yl | H | 107–8 | 63.14 (62.91 | 6.27 6.33 | 19.78 19.81) |
| 44 | Cl | 4-phenylthiazol-2-yl | H | 108–9 | 61.47 (61.87 | 4.64 4.65 | 15.43 15.19) |
| 45 | Cl | 1-(diethoxymethyl)-6-methylbenzimidazol-2-yl | H | Oil | n.m.r. (CDCl₃) δ=3.5 (s, —N—CH₃); 1.25 (t, [O—CH₂CH₃]₂); 3.7 (q, [O—CH₂CH₃]₂) | | |
| 46 | Cl | thiazol-2-yl | CH₃ | 96–97 | 54.83 (54.81 | 4.93 4.93 | 18.00 18.06) |
| 47 | CH₃ | thiazol-2-yl | CH₃ | 105 | 62.66 (62.91 | 6.39 6.34 | 20.17 19.56) |

-continued
$$\underset{R^2}{\overset{CH_3}{\bigcirc}}-N=CH-\overset{CH_3}{\underset{}{N}}-\underset{R^4}{\overset{}{C}}=N\cdot R^3$$
| | R² | | R³ | m.p. (°C) | C | H | N |
|---|---|---|---|---|---|---|---|
| 48 | Cl | 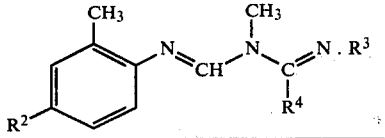 | H | 87–9 | 54.46 (54.81 | 4.88 4.93 | 17.80 18.26) |
| 49 | CH₃ | 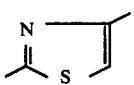 | CH₃ | — | — | — | — |
| 50 | CH₃ | 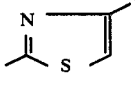 | CH₃ | 68–70 | 64.31 (63.97 | 6.87 6.71 | 19.32 18.65) |
| 51 | Cl | 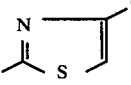 | CH₃ | 77–8 | 55.96 (56.15 | 5.53 5.34 | 21.07 17.46) |
| 52 | CH₃ | 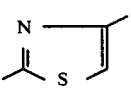 | CH₃ | 99 | 67.90 (68.30 | 6.85 6.81 | 24.29 24.00) |
| 53 | Cl | 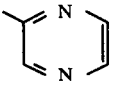 | CH₃ | 124 | 59.30 (59.70 | 5.34 5.34 | 23.13 23.21) |
| 54 | CH₃ | 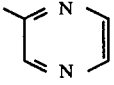 | CH₃ | 145 | 65.04 (65.57 | 7.02 6.80 | 22.24 22.46) |
| 55 | Cl | 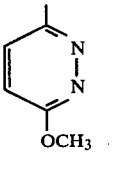 | CH₃ | 149–150 | 57.54 (57.92 | 5.73 5.47 | 21.61 21.00) |
| 56 | Cl | 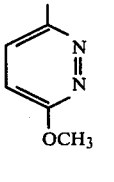 | H | 53 | 50.96 (51.07 | 5.10 5.28 | 32.57 32.07) |
| 57 | CH₃ | 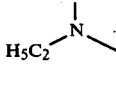 | H | 86 | 58.76 (58.93 | 6.97 6.71 | 35.40 34.36) |
| 58 | CH₃ | 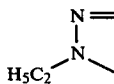 | H | 126–128 | 63.90 (63.97 | 6.67 6.71 | 18.26 18.65) |
| 59 | Cl | 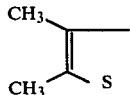 | H | 120–122 | 56.14 (56.15 | 5.31 5.34 | 17.53 17.46) |

-continued
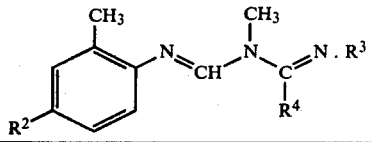
| | $R^2$ | | $R^3$ | m.p. | C | H | N |
|---|---|---|---|---|---|---|---|
| 60 | CH₃ | CH₃-C(=N-)-S-C(CH₃)=C(CH₃) (isopropylidene) | CH₃ | 112–114 | 64.44 (64.94 | 6.92 7.05 | 17.64 17.82) |
| 61 | Cl | CH₃-C(=N-)-S-C(CH₃)=C(CH₃) | CH₃ | 135–6 | 57.22 (57.39 | 5.65 5.72 | 16.64 16.73) |
| 62 | CH₃ | EtO₂C-C(=N-)-S-CH= | H | 121–122 | 59.11 (59.28 | 6.00 5.85 | 16.67 16.27) |
| 63 | Cl | C₆H₅-C(=N-)-S-C(CH₃)= | H | 110–111 | 62.79 (62.74 | 4.78 5.00 | 14.57 14.63) |
| 64 | Cl | C₆H₅-C(=N-)-S-C(CH₃)= | CH₃ | 90–92 | 62.82 (63.54 | 5.41 5.33 | 13.95 13.11) |
| 65 | CH₃ | 3-methyl-2-pyridyl | H | 84–86 | 72.66 (72.83 | 7.12 7.19 | 19.98 19.98) |
| 66 | CH₃ | 6-methyl-2-pyridyl | H | 105–107 | 72.51 (72.83 | 7.08 7.19 | 19.82 19.98) |
| 67 | Cl | 3-methyl-2-pyridyl | H | 92–94 | 63.36 (63.89 | 5.90 5.70 | 18.81 18.63) |
| 68 | CH₃ | 1-isoquinolyl | H | 146–147 | 75.52 (75.92 | 6.49 6.37 | 18.08 17.71) |
| 69 | CH₃ | 4-methyl-2-pyridyl | H | 87–89 | 73.04 (72.83 | 7.40 7.19 | 20.21 19.98) |
| 70 | Cl | 6-methyl-2-pyridyl | H | 103–4 | 64.21 (63.89 | 5.82 5.70 | 19.01 18.63) |
| 71 | Cl | 1-isoquinolyl | H | 124–5 | 67.66 (67.75 | 5.24 5.09 | 16.60 16.63) |

-continued

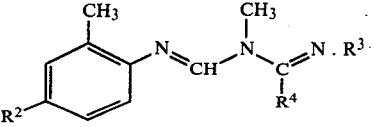

| | | | | | | | |
|---|---|---|---|---|---|---|---|
| 72 | Cl | 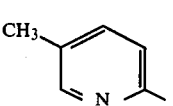 | H | 129–130 | 63.78 (63.89 | 5.77 5.70 | 19.01 18.63) |
| 73 | CH$_3$ | 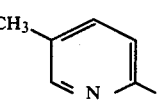 | H | 122–5 | 72.94 (72.83 | 7.13 7.19 | 20.78 19.98) |
| 74 | Cl | 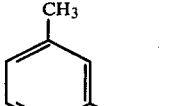 | H | 99.5–101.5 | 64.42 (63.89 | 5.75 5.70 | 18.66 18.63) |
| 75 | CH$_3$ | 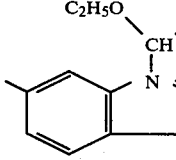 | H | Oil | n.m.r.: δ = 1.23 (t, 6H), 2-CH$_2$CH$_3$; 2.30 (s, 6H) 2 aromatic CH$_3$ groups; 3.53 (s     ) —N . CH$_3$. Molecular weight from mass spectral data <07. | | |

EXAMPLE 76

Preparation of
5-(2,4-Dimethylphenyl)-3-methyl-1-(2-thiazolyl)-1,3,5-triazapenta-1,4-diene

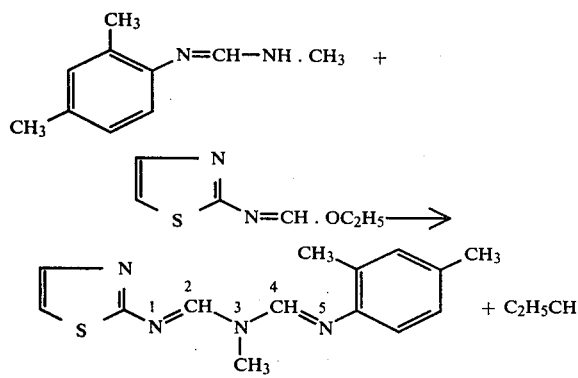

A mixture of N-methyl-N'-(2,4-dimethylphenyl)-formamidine (188.8 g) and ethyl N-(2-thiazolyl)-formimidate (200.0 g) was heated to 75° for 2 hours under water-pump pressure. Ethanol began to distil shortly after heating commenced and ceased after approximately 1 hour. On cooling, the mixture solidified. Crystallisation from n-hexane and recrystallisation from methylene chloride/hexane with decolourising carbon treatment afforded 295 g of product in two crops. (Yield 93%). A portion was further recrystallised from cyclohexane to provide an analytical sample, m.p. 101°.

Analysis %: Found: C, 61.62; H, 5.96; N, 21.23. Calculated for C$_{14}$H$_{16}$N$_4$S: C, 61.73; H, 5.92; N, 20.57%.

The product was identical to the product of Example 18.

EXAMPLE 77–93

The following compounds were prepared similarly to Example 76, starting from N-methyl-N'-(2,4-dimethylphenyl)formamidine and the appropriate formimidate of the formula R$^3$.N=CH.OC$_2$H$_5$.

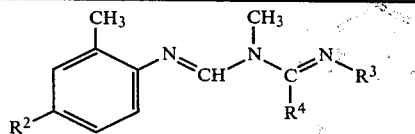

| Compound No. | R$^2$ | R$^3$ | R$^4$ | m.p. (°C.) | Analysis % (Theoretical in brackets) | | |
|---|---|---|---|---|---|---|---|
| | | | | | C (or n.m.r.) | H | N |
| 77 | CH$_3$ |  | H | 134–5 | 67.00 (67.39 | 6.28 6.41 | 27.03 26.20) |

-continued

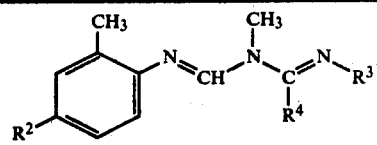

| Compound No. | R² | R³ | R⁴ | m.p. (°C.) | C (or n.m.r.) | H | N |
|---|---|---|---|---|---|---|---|
| 78 | CH₃ | (8-quinolinyl) | H | 89 | 76.34 (75.92 | 6.32 6.37 | 17.7 17.71) |
| 79 | CH₃ | (6-methylbenzothiophene) | H | 64–5 | n.m.r. (CDCl₃) δ = 2.26 (s, 6H), 2 aromatic CH₃ groups; 3.43 (s, 3H), N—CH₃. Molecular weight from mass spectral data 3.21 This compound was a monohydrate. | | |
| 80 | CH₃ | (methylbenzothiazole) | H | oil | 63.51 (63.50 | 5.70 5.92 | 15.51 16.46) |
| 81 | CH₃ | (tetrahydrobenzothiazole) | H | 135 | Molecular weight from mass spectral data 322. 66.04 (66.23 | 6.71 6.79 | 17.24 17.16) |
| 82 | CH₃ | (3,6-dimethyl-2-methylpyridine) | H | 97–8 | 73.14 (73.44 | 7.63 7.53 | 19. 19.03) |
| 83 | CH₃ | (3-ethyl-2-methylpyridine) | H | 91–3 | 75.51 (73.44 | 7.37 7.53 | 18.87 19.03) |
| 84 | CH₃ | (3,5-dichloro-2-methylpyridine) | H | 148–150 | 57.31 (57.32 | 4.56 4.81 | .79 16.71) |
| 85 | CH₃ | (5-bromo-2-methylpyridine) | H | 129 | 55.62 (55.66 | 4.85 4.96 | 16.22 16.23) |
| 86 | CH₃ | (2,4,6-trimethylpyridine) | H | 104 | 73.05 (73.44 | 7.40 7.53 | 1.98 19.03) |
| 87 | CH₃ | (3-propyl-2-methylpyridine) | H | 70–71 | 73.48 (73.99 | 8.10 7.84 | 18.45 18.17) |
| 88 | CH₃ | (3,5-dimethyl-2-methylpyridine) | H | 135–6 | 73.30 (73.44 | 7.32 7.53 | 18.1 19.03) |
| 89 | CH₃ | (3-butyl-2-methylpyridine) | H | 52–3 | 74.14 (74.50 | 8.24 8.13 | 17.06 17.38) |

-continued

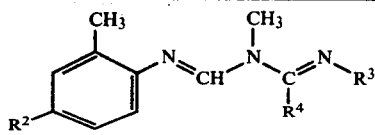

| Compound No. | R² | R³ | R⁴ | m.p. (°C.) | C (or n.m.r.) | H | N |
|---|---|---|---|---|---|---|---|
| 90 | CH₃ | (2-pyridyl) | H | 101 | 72.50 (72.15 | 7.00 6.81 | 2.7 21.04) |
| 91 | CH₃ | (3-quinolyl) | H | 76–79 | n.m.r. (CDC₃) δ = 2.3 (s, 6H-2 Aromatic CH₃'s 3.5 (s, 3H—NCH₃) | | |
| 92 | CH₃ | (4-ethyl-6-methyl-2-pyridyl) | H | 79–80 | 74.12 (74.00 | 7.81 7.84 | 1. 18.17) |
| 93 | CH₃ | (3,4-dimethyl-2-pyridyl) | H | 91 | 73.26 (73.44 | 7.67 7.53 | 18.88 19.03) |

The products of Examples 90 to 92 were identical to the products of Examples 1,2 and 16 respectively.

EXAMPLE 94

The constituents of an emulsifiable concentrate are as follows:

| | |
|---|---|
| 5-(2,4-Dimethylphenyl)-3-methyl-1-(2-pyridyl)-1,3,5-triazapenta-1,4-diene | 5–75% w/v |
| Emulsifier(s) | up to 20% w/v |
| Antioxidant(s) | up to 0.1% |
| Mixed hydrocarbon solvent | balance to 100% |

The concentrate is prepared by mixing the emulsifier(s), antioxidant(s) and solvent until homogeneous, adding the triazapentadiene and stirring until dissolution occurs.

Preparation of Starting Materials

The following examples, in which all temperatures are in °C., illustrate the preparation of certain of the starting materials:

EXAMPLE I

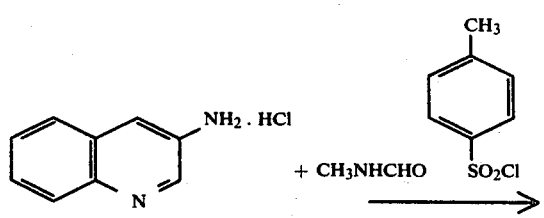

-continued

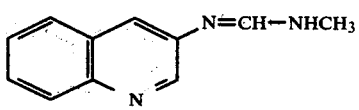

A solution of 3-aminoquinoline (5.8 g, 0.04 m) in dry ether was treated with hydrogen chloride gas and the resulting monohydrochloride salt obtained by filtration. A suspension of this salt and p-toluenesulphonyl chloride (7.2 g, 0.038 m) in N-methylformamide (30 ml) was stirred at room temperature for 30 minutes then warmed to 90° on a steam bath. After 1 hour, the resulting yellow suspension was cooled and poured into acetone (100 ml), and the insoluble solid filtered off. The solid was then dissolved in water, the resulting solution basified with 10N NaOH solution, and the resulting solid extracted into chloroform. The chloroform extract was dried and the solvent removed in vacuo to yield an almost colourless solid which crystallised from chloroform/40°–60° petroleum ether to give N-methyl-N'-(3-quinolyl)-formamidine, (5.5 g, 95%) of m.p. 142°–143°.

Analysis: Found: C, 71.08; H, 5.78; N, 22.99%. Required for $C_{11}H_{11}N_3$: C, 71.30; H, 5.98; N, 22.67%.

EXAMPLES II TO V

The following formamidines were prepared by procedures similar to that of Example I, starting with N-methylformamide and the appropriate amine of the formula $R^3.NH_2$.

| | R³.N=CH—NH.CH₃ | | | |
|---|---|---|---|---|
| | | m.p. | n.m.r. or Analysis % (Theoretical in brackets) | |
| Compound | R³ | (°C.) | C H N | |
| II | 3-pyridyl | oil | n.m.r. (CDCl₃): δ = 3.00 (s, —N.CH₃), 6.3 (s, NH.CH₃) 7.66 (s, —N=CH—N). | |
| III | 2,6-dimethyl-pyridin-3-yl (CH₃, N, CH₃) | 142–144 | 66.07  8.17  25.19 (66.23  8.03  25.74) | |
| IV | 2-chloropyridin-3-yl (N, Cl) | 106–9 | 49.37  4.61  24.62 (49.57  4.75  24.77) | |
| V | 2,6-dimethoxy-pyridin-3-yl (CH₃O, N, OCH₃) | 105–6 | 54.67  6.52  21.30 (55.37  6.71  21.52) | |

EXAMPLE VI

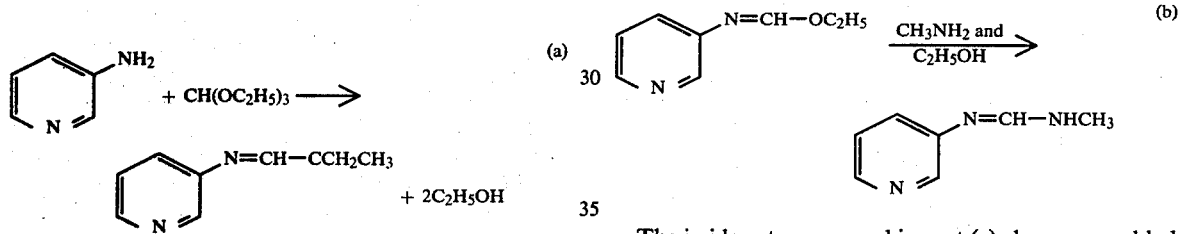

A solution of 3-aminopyridine (20.0 g, 0.21 m) in excess triethyl orthoformate (100 ml) and ethanolic hydrogen chloride (0.3 ml) was heated under reflux for 72 hours. Ethanol and excess triethyl orthoformate were then removed by distillation over a period of 5 hours. Solid potassium carbonate (100 mg) was added to the residue, and the last traces of triethyl orthoformate were removed in vacuo. The residue was then distilled under reduced pressure to yield the desired imido ester, ethyl N-(3-pyridyl)-formimidate, as a colourless liquid, (b.p. 62°/0.5 mm) (24 g, 75%), n.m.r. (CDCl₃): δ=1.4 (t, —CH₂CH₃), 4.32 (q, —CH₂CH₃), 7.73 (s, —N=CH—O).

The preparation of this compound is also described in J. Prakt. Chem., 313, 179 (1971).

The imido ester prepared in part (a) above was added to a solution of methylamine in ethanol (33% w/w) at −10°, and the resulting solution was then allowed to attain room temperature (25°). After standing overnight, the solvent and excess methylamine were removed at 40° in vacuo to yield the N-methyl-N'-(3-pyridyl) formamidine (15 g) as a colourless liquid. n.m.r. (CDCl₃); δ=3.00 (s, —N.CH₃), 7.66 (S, —N—CH—N).

The preparation of this compound is also described in J. Prakt. Chem., 314, 627 (1972).

EXAMPLES VII TO LVIII

The following imido esters were prepared by procedures similar to that of Example VI part (a), starting from the appropriate amine of the formula R³.NH₂ and ester of the formula R⁴.C(OC₂H₅)₃.

| | R³.N=C(—OC₂H₅)(R⁴) | | | |
|---|---|---|---|---|
| Compound | R³ | R⁴ | B.P. (°C.) | n.m.r. |
| VII* | 3-pyridyl | H | 60°/2mm | n.m.r. (CDCl₃): δ = 1.4 (t, —CH₂CH₃), 4.40 (q, —CH₂CH₃), 8.32 (s, —N=CH—O) |
| VIII* | 4-pyridyl | H | 66°/0.5 mm | n.m.r. (CDCl₃): δ = 1.35 (t, —CH₂CH₃), 4.35 (q, —CH₂CH₃), 7.72 (s, —N=CH—O) |

-continued $$R^3 \cdot N=\underset{R^4}{C}-OC_2H_5$$

| Compound | R³ | R⁴ | B.P. (°C.) | n.m.r. |
|---|---|---|---|---|
| IX | 3-pyridyl | CH₃ | 64°/ 0.5 mm | n.m.r. (CDCl₃): δ = 1.35 (t, —CH₂CH₃), 4.25 (q, —CH₂CH₃), 1.87 (s, C—CH₃) |
| X | 3-pyridyl | C₂H₅ | 70°/ 0.4 mm | n.m.r. (CDCl₃): δ = 1.35 (t, —OCH₂CH₃), 4.25 (q, —OCH₂CH₃), 2.15 (q, C—CH₂CH₃), 1.10 (t, —C . CH₂CH₃) |
| XI* | 5-chloro-2-pyridyl | H | 66°/ 0.1 mm | n.m.r. (CDCl₃): δ = 1.38 (t, —CH₂CH₃), 4.35 (q, —CH₂CH₃), 8.32 (s, —N=CH—O) |
| XII | 3-ethyl-6-methyl-2-pyridyl | H | 60°/ 0.1 mm | n.m.r. (CDCl₃): δ = 1.4 (t, —OCH₂CH₃), 4.38 (q, —OCH₂CH₃), 8.25 (s, —N=CH—O) |
| XIII | 2,6-dichloro-pyridyl | H | 120°/ 0.22 mm | n.m.r. (CDCl₃): δ = 1.4 (t, —CH₂CH₃), 4.4 (q, —CH₂CH₃), 7.7 (s, —N=CH—O) |
| XIV | thiazolyl | H | 56°/ 0.08 mm | n.m.r. (CDCl₃): δ = 1.25 (t, —CH₂CH₃), 4.30 (q, —CH₂CH₃), 8.3 (s, —N—CH—O) |
| XV | benzothiazolyl | H | 60°-62° (m.p.) | n.m.r. (CDCl₃): δ = 1.4 (t, —CH₂CH₃), 4.45 (q, —CH₂CH₃), 8.4 (s, —N=CH—O) |
| XVI | 4,5-dimethylthiazolyl | CH₃ | 88° @ 0.2 mm | n.m.r. (CDCl₃) δ = 1.3 (t, —CH₂CH₃) 4.25 (q, —CH₂CH₃) 2.1 (s, —C—CH₃) |
| XVII | (EtO)₂CH–N indazolyl-6-methyl | H | 165° @ 0.05 mm | n.m.r. (CDCl₃) δ = 1.4 (t, CH₂CH₃) 4.3 (q, CH₂CH₃) 1.2 (t, [O—CH₂CH₃]₂) 3.65 (q, [OCH₂CH₃]₂) |
| XVIII | 6-methylquinoxalinyl | H | MPt. 85° | n.m.r. (CDCl₃) δ = 1.4 (t, CH₂CH₃) 4.4 (q, CH₂CH₃) |
| XIX | 4-phenylthiazolyl | CH₃ | 145° @ 0.3 mm | n.m.r. (CDCl₃) δ = 1.3 (t, —CH₂CH₃) 4.3 (q, —CH₂CH₃) 2.2 (s, —C—CH₃) |
| XX | 4-methylthiazolyl | CH₃ | 78° @ 0.1 mm | n.m.r. (CDCl₃) δ = 1.3 (t, —CH₂CH₃) 4.3 (q, —CH₂CH₃) 2.2 (s, —C—CH₃) |
| XXI | pyrazinyl | CH₃ | 54°-6° @ 0.1 mm | n.m.r. (CDCl₃) δ = 1.4 (t, —CH₂CH₃) 4.3 (q, —CH₂CH₃) 2.0 (s, —C—CH₃) |
| XXII | 4-(ethoxycarbonyl)thiazolyl | H | 143°-7° @ 0.3 mm | n.m.r. (CDCl₃) δ = 1.4 (t, CH₂CH₃) 4.4 (q, CH₂CH₃) 8.45 (s, N=CH—O) |

-continued $$R^3 \cdot N=C-OC_2H_5$$
$$\quad\quad\quad\, |$$
$$\quad\quad\quad R^4$$

| Compound | R³ | R⁴ | B.P. (°C.) | n.m.r. |
|---|---|---|---|---|
| XXIII | 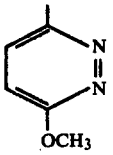 | CH₃ | MPt. 81°–2° | n.m.r. (CDCl₃) δ = 1.35 (t, CH₂CH₃) 4.3 (q, CH₂CH₃) 2.0 (s, C—CH₃) |
| XXIV | 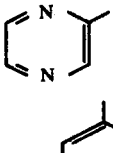 | H | 87°–8° @ 2 mm | n.m.r. (CDCl₃) δ = 1.35 (t, CH₂CH₃) 4.4 (q, CH₂CH₃) |
| XXV | 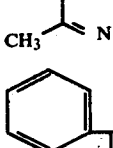 | CH₃ | 86°–8° @ 0.1 mm | n.m.r. (CDCl₃) δ = 1.35 (t, CH₂CH₃) 4.25 (q, CH₂CH₃) 1.85 (s, —C—CH₃) |
| XXVI | 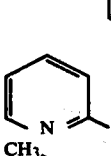 | H | 156°–62° @ 0.05 mm | n.m.r. (CDCl₃) δ = 1.3 (t, CH₂CH₃) 4.3 (q, CH₂CH₃) 8.4 (s, N=CH—O) |
| XXVII | 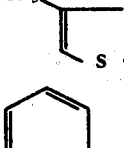 | CH₃ | 57°–60° @ 0.01 mm | n.m.r. (CDCl₃) δ = 1.3 (t, CH₂CH₃) 4.25 (q, CH₂CH₃) 1.8 (s, C—CH₃) |
| XXVIII | 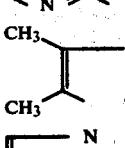 | H | 74° @ 0.1 mm | n.m.r. (CDCl₃) δ = 1.4 (t, CH₂CH₃) 4.4 (q, CH₂CH₃) 8.3 (s, N=CH—O) |
| XXIX | 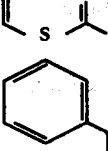 | CH₂CH₃ | 57°–60° @ 0.1 mm | n.m.r. (CDCl₃) δ = 1.4 (t, OCH₂CH₃) 4.3 (q, OCH₂CH₃) 1.1 (t, C—CH₂CH₃) 1.5 (q, C—CH₂CH₃) |
| XXX | 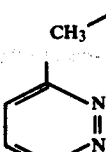 | H | 86°–90° @ 0.2 mm | n.m.r. (CDCl₃) δ = 1.3 (t, CH₂CH₃) 4.3 (q, CH₂CH₃) 8.1 (s, N=CH—O) |
| XXXI | 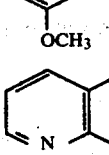 | CH₃ | 60° @ 0.1 mm | n.m.r. (CDCl₃) δ = 1.3 (t, CH₂CH₃) 4.3 (q, CH₂CH₃) 2.1 (s, C—CH₃) |
| XXXII | 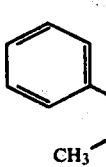 | CH₃ | 142°–4° @ 0.35 mm | n.m.r. (CDCl₃) δ = 1.3 (t, CH₂CH₃) 4.3 (q, CH₂CH₃) 2.2 (s, —C—CH₃) |
| XXXIII |  | H | 86° @ 0.02 mm | n.m.r. (CDCl₃) δ = 1.4 (t, CH₂CH₃) 4.4 (q, CH₂CH₃) 8.4 (s, N=CH—O) |
| XXXIV |  | H | 136° @ 0.1 mm | n.m.r. (CDCl₃) δ = 1.4 (t, CH₂CH₃) 4.35 (q, CH₂CH₃) 8.1 (s, N=CH—O) |
| XXXV | 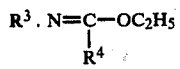 | H | 156°–160° @ 0.03 mm | n.m.r. (CDCl₃) δ = 1.35 (t, CH₂CH₃) 4.35 (q, CH₂CH₃) 8.3 (s, N=CH—O) |

-continued $R^3 \cdot N=C-OC_2H_5$
         $|$
         $R^4$

| Compound | R³ | R⁴ | B.P. (°C.) | n.m.r. |
|---|---|---|---|---|
| XXXVI | 3,6-dimethoxy-5-methyl-2-pyridyl (OCH₃, N, OCH₃ with C-CH₃) | CH₃ | 96°–100° @ 0.025 mm | n.m.r. (CDCl₃) δ = 1.35 (t, CH₂CH₃) 4.25 (q, CH₂CH₃) 1.8 (s, C—CH₃) |
| XXXVII | 4-methyl-2,6-dimethylpyridyl | H | 76°–82° @ 0.05 mm | n.m.r. (CDCl₃) δ = 1.35 (t, CH₂CH₃) 4.3 (q, CH₂CH₃) 7.65 (s, N=CH—O) |
| XXXVIII | 1-ethyl-1,2,4-triazol-3-yl | H | 88°–90° @ 0.4 mm | (C, H and N analyses - theoretical in brackets) 42.97 6.58 41.62 (42.60 6.55 41.39) |
| XXXIX | 1-[α,α-bis(ethoxy)methyl]-5-methylbenzimidazol-2-yl | H | 150°–2° @ 0.01 mm | n.m.r. δ = 7.80 (s, —N=CH); 4.30 (q, —OCH₂CH₃) 1.35 (t, —OCH₂CH₃) 3.50 (q, —CH(OCH₂ CH₃)₂); 1.18 (t, —CH(OCH₂ CH₃)₂. Molecular wt. from mass spectra 291. |
| XL | 3-methyl-2-pyridyl | H | 82° @ 0.75 mm | n.m.r. (CDCl₃) δ = 8.24 (s, N=CH—O), 4.40 (q, —OCH₂CH₃); 8.3 (s, Ar—CH₃; 1.4 (t, —OCH₂CH₃). |
| XLI | 6-methyl-2-pyridyl | H | 70°–72° @ 0.4 mm | n.m.r. (CDCl₃) δ = 8.23 (s, N=CH—O); 4.39 (q, —OCH₂CH₃); = 2.5 (s, Ar—CH₃); 1.39 (t, —OCH₂CH₃). |
| XLII | 4-methyl-2-pyridyl | H | 90°–92° @ 0.6–0.7 mm | n.m.r. (CDCl₃) δ = 8.31 (s, N=CH—O); 4.40 (q, —OCH₂CH₃); = 2.34 (s, Ar—CH₃); 1.40 (t, —OCH₂CH₃). |
| XLIII | 5-methyl-2-pyridyl | H | 80°–82° @ 0.7 mm | n.m.r. (CDCl₃) δ = 8.3 (s, —N=CH—O); 4.28 (q, —OCH₂CH₃); = 2.18 (s, Ar—CH₃); 1.29 (t, —OCH₂CH₃). |
| XLIV | 1-isoquinolyl | H | 128° @ 0.05 mm | n.m.r. (CDCl₃) δ = 8.41 (s, N=CH—O); 4.52 (q, —OCH₂CH₃); = 1.46 (t, —OCH₂CH₃). |
| XLV | 2-pyrimidyl | H | 84° @ 0.5 mm | n.m.r. (CDCl₃) δ = 8.58 (s, —N=CH—O); 4.48 (q, —OCH₂CH₃); = 1.38 (t, —OCH₂CH₃). |
| XLVI | benzothiazol-2-yl | H | 132° @ 0.4 mm | n.m.r. (CDCl₃) δ = 7.8 (s, —N=CH—O); 4.4 (q, —OCH₂CH₃); = 1.4 (t, —OCH₂CH₃). |
| XLVII | 3,5-dimethyl-2-pyridyl | H | 70° @ 0.4 mm | n.m.r. (CDCl₃) δ = 8.16 (s, —N=CH—O); 4.36 (q, —OCH₂CH₃) = 2.42 (s, Ar—CH₃); 2.21 (s, Ar—CH₃); = 1.36 (t, —OCH₂CH₃). |
| XLVIII | 3-ethyl-2-pyridyl | H | 66° @ 0.3 mm | n.m.r. (CDCl₃) δ = 8.39 (s, —N=CH—O); 4.52 (q, —OCH₂CH₃) = 2.56–3.09 (m, Ar—CH₂CH₃); 1.55 (t, Ar—CH₂CH₃); = 1.39 (t, —OCH₂CH₃). |

-continued $$R^3 . N=C-OC_2H_5$$
$$\phantom{R^3 . N=}|$$
$$\phantom{R^3 . N=}R^4$$

| Compound | R³ | R⁴ | B.P. (°C.) | n.m.r. |
|---|---|---|---|---|
| XLIX | 3,5-dichloro-2-pyridyl | H | 72° @ 0.1 mm | n.m.r. (CDCl₃) $\delta$ = 8.34 (s, —N=CH—O); 4.55 (q, —CH₂CH₃); = 1.55 (t, —CH₂CH₃). |
| L | 5-bromo-2-pyridyl | H | 75°–80° @ 0.2 mm | n.m.r. (CDCl₃) $\delta$ = 8.32 (s, —N=CH—O); 4.35 (q, —CH₂CH₃); = 1.35 (t, —CH₂CH₃). |
| LI | 3-propyl-2-pyridyl (CH₂CH₂CH₃) | H | 93° @ 0.2 mm | n.m.r. (CDCl₃) $\delta$ = 8.29 (s, —N=CH—O); 4.38 (q, —OCH₂CH₃) = 1.39 (t, —OCH₂CH₃). |
| LII | 4,5,6,7-tetrahydrobenzothiazol-2-yl | H | 60°–62° (m.p.) | n.m.r. (CDCl₃) $\delta$ = 8.44 (s, —N=CH—O); 4.45 (q, —OCH₂CH₃); = 1.4 (t, —OCH₂CH₃). |
| LIII | 3,5-dimethyl-2-pyridyl | H | 100°–120° @ 14 mm | n.m.r. (CDCl₃) $\delta$ = 8.2 (s, —N=CH—O); 4.30 (q, —OCH₂CH₃); = 2.16 (s, Ar—CH₃); 1.29 (t, —CH₂CH₃). |
| LIV | 3-quinolyl | H | 127° @ 0.5 mm | n.m.r. (CDCl₃) $\delta$ = 7.7 (s, —N=CH—O); 4.3 (q, —OCH₂CH₃); = 1.3 (q, —OCH₂CH₃). |
| LV | 3-butyl-2-pyridyl ((CH₂)₃CH₃) | H | 93° @ 0.2 mm | n.m.r. (CDCl₃) $\delta$ = 8.29 (s, —N=CH—O); 4.38 (q, —OCH₂CH₃); = 1.39 (t, —OCH₂CH₃). |
| LVI | 3,4-dimethyl-2-pyridyl | H | 86°–88° @ 0.4 mm | n.m.r. (CDCl₃) $\delta$ = 8.24 (s, —N=CH—O); 3.57 (q, —OCH₂CH₃); = 2.2 (s, 2 Aromatic CH₃'s); = 1.2 (t, —OCH₂CH₃). |
| LVII | 8-quinolyl | H | 102°–104° @ 0.25 mm | n.m.r. (CDCl₃) $\delta$ = 7.96 (s, —N=CH—O); 4.52 (q, —OCH₂CH₃); 1.4 (t, —OCH₂CH₃). |
| LVIII | benzothiophenyl | H | 102° @ 0.1 mm | n.m.r. (CDCl₃) $\delta$ = 7.66 (s, —N=CH—O); 4.28 (q, —OCH₂CH₃); 1.32 (t, —OCH₂CH₃). |

*the preparation of these compounds are also described in T. Prakt. Chem., 313, 179 (1979).

EXAMPLE LIX TO XCVI

The following amidines were prepared by procedures similar to that of Example VI part (b), starting from the appropriate imido ester of the formula R³.N=C(R⁴)OC₂H₅ and methylamine.

$$R^3 . N=C(R^4) . NHCH_3$$

| Compound | R³ | R⁴ | M.P. (°C.) | n.m.r. or Analysis % (Theoretical in brackets) C H N |
|---|---|---|---|---|
| LIX | 2-pyridyl* | H | — | n.m.r.(CDCl₃): $\delta$ = 2.95 (s, —N . CH₃), 8.45 (s, —N=CH—N) |

-continued

| | | | M.P. | n.m.r. or Analysis % (Theoretical in brackets) | | |
|---|---|---|---|---|---|---|
| Compound | R³ | R⁴ | (°C.) | C | H | N |
| LX | 4-pyridyl | H | — | n.m.r. (CDCl₃): δ = 3.02 (s, —N . CH₃), 7.80 (s, —N=CH—N) | | |
| LXI | 3-pyridyl | CH₃ | — | n.m.r. (CDCl₃): δ = 2.85 (s, —N . CH₃), 1.80 (s, N=C—CH₃), 6.3 (s, NHCH₃) | | |
| LXII | 3-pyridyl | C₂H₅ | — | n.m.r. (CDCl₃): δ = 2.90 (s, —N . CH₃), 2.20 (q, —CH₂CH₃), 1.05 (t, —CH₂CH₃) | | |
| LXIII | 5-chloro-2-pyridyl | H | 112° | n.m.r. (CDCl₃): δ = 3.02 (s, —N . CH₃), 8.42 (s, —N=CH—N) | | |
| LXIV | 6-methyl-3-ethyl-2-pyridyl | H | — | n.m.r. (CDCl₃): δ = 3.00 (s, —N . CH₃), 8.35 (s, —N=CH—N) | | |
| LXV | 2,6-dichloro-3-methylpyridyl | H | 134-5° | 40.96 (41.20) | 3.42 (3.46) | 20.87 (20.59) |
| LXVI | thiazolyl | H | 84-85° | 42.70 (42.54) | 5.09 (5.00) | 29.69 (29.76) |
| LXVII | benzothiazolyl | H | 132° | n.m.r. (CDCl₃): δ = 3.10 (s, —N . CH₃), 8.40 (s, —N=CH—N) | | |
| LXVIII | 4-phenyl-5-methylthiazolyl | CH₃ | 129-130° | 63.86 (63.64) | 6.46 (6.16) | 16.63 (17.13) |
| LXIX | 4,5-dimethylthiazolyl | H | 129-131° | 49.63 (49.68) | 6.40 (6.55) | 25.09 (24.83) |
| LXX | N-(2,6-diethoxymethyl)tolyl | H | oil | n.m.r. (CDCl₃) δ = 3.0 (s, NH—CH₃) 7.9 (s, N=CH—NH) 1.2 (t, [O—CH₂CH₃]₂) 3.6 (q, [O—CH₂CH₃]₂) | | |
| LXXI | 6-methylquinoxalinyl | H | MPt. 118° | n.m.r. (CDCl₃) δ = 3.05 (s, NH—CH₃) | | |
| LXXII | 4-phenylthiazolyl | CH₃ | 101-3° | 62.85 (62.31) | 5.77 (5.66) | 18.44 (18.17) |
| LXXIII | 4-methylthiazolyl | CH₃ | 60-2° | 49.62 (49.68) | 6.44 (6.55) | 25.39 (24.83) |

-continued

R³.N=C(R⁴).NHCH₃

| Compound | R³ | R⁴ | M.P. (°C.) | n.m.r. or Analysis % (Theoretical in brackets) C H N |
|---|---|---|---|---|
| LXXIV | 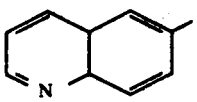 | H | Oil | n.m.r. (CDCl₃) δ = 3.0 (s, NH—CH₃) |
| LXXV |  | C₂H₅ | BPt. 90° @ 0.04 mm | n.m.r. (CDCl₃) δ = 2.95 (d, NH—CH₃) 1.25 (t, C—CH₂CH₃) 2.4 (q, C—CH₂CH₃) |
| LXXVI |  | CH₃ | BPt. 90° @ 0.03 mm | n.m.r. (CDCl₃) δ = 3.1 (d, NH—CH₃) 2.9 (s, C—CH₃) |
| LXXVII |  | CH₃ | 78° | 46.25 5.91 26.74 (46.43 5.85 27.07) |
| LXXVIII | 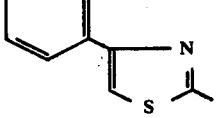 | H | 106–8° | 61.31 5.17 18.98 (60.80 5.10 19.34) |
| LXXIX | 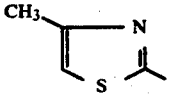 | H | 129–131° | 46.81 6.07 27.38 (46.43 5.84 27.07) |
| LXXX | 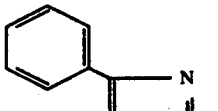 | H | 145–6° | 61.99 5.52 18.16 (62.31 5.66 18.17) |
| LXXXI | 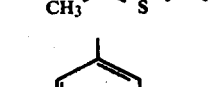 | CH₃ | 153–6° | 67.66 8.60 24.20 (67.76 8.53 23.71) |
| LXXXII | 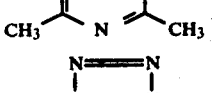 | H | 81–82° | 39.08 6.56 54.57 (38.95 6.54 54.51) |
| LXXXIII | 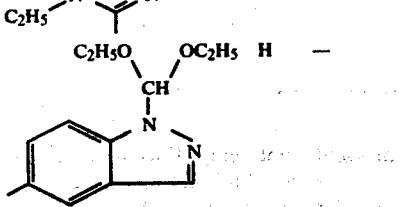 | H | — | n.m.r. δ = 7.88 (s, —N=CH) 2.95 (s, —N—CH₃); 3.60 (q, CH(OCH₂CH₃)₂); 1.21 (t, CH(OCH₂CH₃)₂). Molecular weight from mass spectra: 276. |
| LXXXIV | 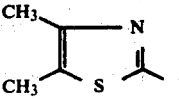 | CH₃ | 77–80° | 51.71 6.74 23.08 (52.43 7.15 22.93) |
| LXXXV | 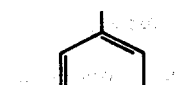 | H | | |
| LXXXVI | 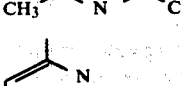 | H | | |

-continued $$R^3 . N=C(R^4) . NHCH_3$$

| Compound | R³ | R⁴ | M.P. (°C.) | n.m.r. or Analysis % (Theoretical in brackets) C H N |
|---|---|---|---|---|
| LXXXVII | (methylpyrazinyl) | H | | These formamidines were not characterised, being used directly in the preparation of the triazapentadiene product. |
| LXXXVIII | (3-methyl-2,6-dimethoxypyridinyl) | CH₃ | | |
| LXXXIX | (methylpyrazinyl) | CH₃ | | |
| XC | (6-methoxypyrimidin-4-yl with methyl) | CH₃ | | |
| XCI | C₂H₅O₂C—thiazolyl | H | | |
| XCII | (3-methylpyridin-2-yl) | H | oil | Not characterised. Used directly in the preparation of the triazapentadiene. |
| XCIII | (6-methylpyridin-2-yl with CH₃) | H | 82–84 | 64.20 7.41 28.32 (64.40 7.43 28.16) |
| XCIV | (4-methylpyridin-2-yl) | H | oil | Not characterised. Used directly in the preparation of the triazapentadiene. |
| XCV | (5-methylpyridin-2-yl) | H | 82–84 | 64.41 7.37 28.50 (64.40 7.43 28.16) |
| XCVI | (isoquinolin-1-yl) | H | 81–83 | 71.17 6.00 22.25 (71.33 5.99 22.69) |

*The preparation of these compounds is also described in J. Frakt. Chem., 314, 627 (1972)

What is claimed is:

1. A triazapentadiene of the formula:

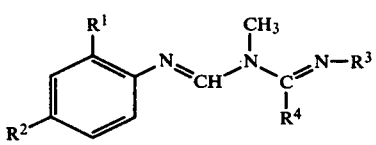

and the acaricidally acceptable acid addition salts thereof, wherein

R¹ is alkyl of 1 to 4 carbon atoms;
R² is selected from the group consisting of hydrogen, chlorine, bromine, fluorine, iodine and alkyl of 1 to 4 carbon atoms;
R³ is benzothiazolyl or thiazolyl optionally containing one or two substituents selected from the group consisting of alkyl of 1 to 4 carbon atoms, alkoxycarbonyl containing 1 to 4 carbon atoms in the alkoxy moiety and unsubstituted phenyl; and
R⁴ is hydrogen or alkyl of 1 to 4 carbon atoms.

2. A triazapentadiene according to claim 1 wherein R¹ is a methyl group.
3. A triazapentadiene according to claim 1 wherein R² is a methyl group.
4. A triazapentadiene according to claim 1 wherein R² is a chlorine atom.
5. An acaricidal composition comprising an acaricidally effective amount of a compound of claim 1 and a diluent or carrier.
6. A method of combatting ectoparasites on animals, which comprises contacting said animals with an acaricidally effective amount of a compound of claim 1.
7. 5-(2,4-dimethylphenyl)-3-methyl-1-(6-benzothiazolyl)-1,3,5-triazapenta-1,4-diene.
8. 5-(2,4-dimethylphenyl)-3-methyl-1-(2-thiazolyl)-1,3,5-triazapenta-1,4-diene.

* * * * *